United States Patent [19]

Bargenda et al.

[11] 4,149,526

[45] Apr. 17, 1979

[54] METHOD OF MEASURING THE HEART PULSE FREQUENCY AND HEART PULSE FREQUENCY METER APPARATUS

[75] Inventors: Siegfried Bargenda, Rockenhausen; Friedrich Arnold, Reutlingen; Richard Häussermann, Pfullingen, all of Fed. Rep. of Germany

[73] Assignee: Keiper Trainingsysteme GmbH & Co., Rockenhausen, Fed. Rep. of Germany

[21] Appl. No.: 726,763

[22] Filed: Sep. 27, 1976

[30] Foreign Application Priority Data

Oct. 1, 1975 [DE] Fed. Rep. of Germany ....... 2543713
Jul. 1, 1976 [DE] Fed. Rep. of Germany ....... 2629517

[51] Int. Cl.² ............................................. A61B 5/04
[52] U.S. Cl. ............................................. 128/2.06 F
[58] Field of Search ................ 128/2.05 P, 2.05 R, 128/2.06 B, 2.06 F, 2.1 R; 235/150.3, 183; 324/78 D, 78 Z

[56] References Cited

U.S. PATENT DOCUMENTS

| 3,171,892 | 3/1965 | Pantle | 128/2.05 R X |
| 3,318,303 | 5/1967 | Hammacher | 128/2.05 S |
| 3,572,324 | 3/1971 | Petersen | 128/2.06 B |
| 3,608,545 | 9/1971 | Novack et al. | 128/2.06 F |
| 3,638,001 | 1/1972 | Gordon | 324/78 D X |
| 3,717,140 | 2/1975 | Greenwood | 128/2.05 T |
| 3,750,644 | 8/1973 | Ragsdale | 128/2.06 R X |
| 3,809,874 | 5/1974 | Pozzetti et al. | 235/183 |
| 3,936,663 | 2/1976 | Taylor et al. | 235/183 X |

FOREIGN PATENT DOCUMENTS 2352692 4/1975 Fed. Rep. of Germany.
1589557 3/1970 France.
2192789 2/1974 France.

OTHER PUBLICATIONS

Dvorak et al., "Elektronik" part 9, 1975, pp. 100-102 and 106.

Primary Examiner—William E. Kamm
Attorney, Agent, or Firm—Wigman & Cohen

[57] ABSTRACT

A method of and apparatus for measuring the heart pulse frequency, especially that of a moving test person for the purpose of a performance test, are disclosed. The mean value of the heart pulse frequency is determined from a measurement of the number of counted pulses of constant frequency which falls within a period of time defined by a predetermined number n of heart pulse periods E whereby the sum of the counted pulses is formed of three terms of a sum, the first term of which corresponds to the sum of the counted pulses within the period of time $-1$ to $n-1$, the second term of which corresponds to the negative value of the first term divided by the predetermined number n of heart pulse periods and the third term of which corresponds to the number of counted pulses within the period of time of $n-1$ to n. Signals detected at the body of a test person are amplified as a function of the peak value of the preceding signal and stored for a short time until the next signal is received. The amplified signals are used to trigger a threshold value switch feeding a monostable multivibrator which aids in eliminating interfering signals.

14 Claims, 3 Drawing Figures

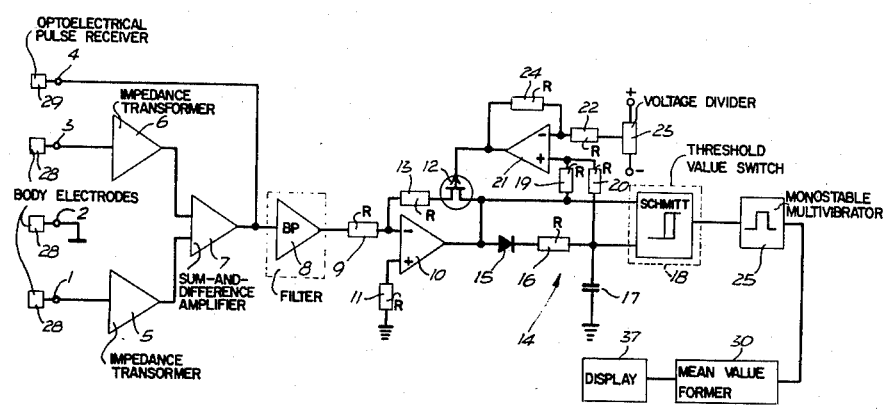

METHOD OF MEASURING THE HEART PULSE FREQUENCY AND HEART PULSE FREQUENCY METER APPARATUS

BACKGROUND OF THE INVENTION

The invention concerns a process for the measuring of the heart pulse frequency, particularly for the measuring of the heart pulse frequency of a moving test person for the purpose of a performance test as well as a heart pulse frequency meter.

The measuring of the heart pulse frequency with the known processes and units is generally unsatisfactory, at least when the test person moves during the measuring process as is the case during a performance test. In particular, the accuracy is unsatisfactory, but, in addition, interfering influences are not eliminated to a sufficient degree.

SUMMARY AND OBJECTS OF THE INVENTION

An object of the invention is to provide a process and apparatus for the measuring of the heart pulse frequency wherein interfering influences are eliminated, for example, interference pulses, for supplying accurate values and which requires an easily effected, simple adjustment to the test person. This object is performed according to the invention by the fact that the mean value of the heart pulse frequency is determined from that number of counted pulses of constant frequency which falls into a period of time defined by a predetermined number n of heart pulse periods E whereby the sum of the counted pulses is formed of three terms of a sum, the first term of which corresponds to the sum of the counted pulses within the period of time $-1$ to $n-1$, the second term to the negative value of the first term divided by the predetermined number n of heart pulse periods and the third term to the number of counted pulses within the period of time $n-1$ to n. The sliding mean value determined in this manner, which is always determined from the number of counted pulses which has fallen into the period of time of the $n+1$ heart pulse periods terminated at the moment of the measuring, is very accurate. Another considerable advantage of the process according to the invention consists of the fact that the computation of this sliding mean value with the aid of an arithmetic computer with program storage requires a relatively low expenditure since only two storage spaces are necessary.

In order to eliminate interfering influences, it is advantageous to eliminate changes of the mean value of the heart pulse frequency within a heart pulse period of more than a single unit.

In order to reliably pick up each signal produced by a pulse beat, in the case of a preferred embodiment, the signals taken from the body of the test person are amplified as a function of the peak value of the preceding signal and subsequently stored until the next signal occurs. Furthermore, a threshold value switch is triggered by means of the amplified signals.

Owing to the amplification of the signals as a function of the peak value of the preceding signal, fluctuations of the signal volume, which are due to interferences when picking up the signals by means of the receiver, can be eliminated to a sufficient degree. The peak value of the amplified signal is, therefore, in a predetermined range and is thus in a position to trigger a subsequent threshold value switch. The triggering of this threshold value switch due to the peak value of the amplified signal leads, furthermore, to the elimination of interference signals. In this way it is thus insured that, with each pulse beat, the threshold value switch and a pulse shaper circuit, which is preferably arranged subsequent to it, are triggered which results in a sequence of pulses corresponding to the pulse beats in a selective form and magnitude.

For reasons of expediency, the signals are additionally filtered. For this purpose, it is advantageous to eliminate pulse signals the period of which is smaller than 80% and larger than 120% of the period of the preceding pulse signal, i.e., which do not meet the condition $0.8\ E_{n-1} < E_n < 1.2\ E_{n-1}$ and to not take into account when forming the mean value, those pulse signals whose period duration is outside the predetermined limits, preferably below 0.2 second and above 2 seconds.

The invention is also based on an object to provide a heart pulse frequency meter to perform the process according to the invention which is of as simple a design as possible but is, nevertheless, operationally reliable. This object is accomplished according to the invention by a receiver which produces a sequence of electrical signals due to the pulse beats with amplification by a subsequent amplifier, a counting pulse generator with constant pulse frequency, a device for the formation of the mean value which determines the mean value of the pulse frequency over a period of time of n heart pulse periods owing to the number of counted pulses falling into this period of time, counters which determine the counted impulses falling into the period of time $-1$ to $n-1$ and $n-1$ to n as well as a calculator circuit which deducts from the sum of the number of pulses counted by the two counters with the nth part of the number of counted pulses within the period of time $-1$ to $n-1$.

In the case of a preferred embodiment, the amplifier subsequent to the receiver is designed as an amplifier with variable amplification subsequent to which a threshold value switch as well as a short-time storage are installed to which a control circuit for the control of the amplification is connected. Preferably, a monostable multivibrator is connected to the output of the threshold value switch, the unstable state of which is, in the case of a preferred embodiment, adjusted at a period of time which permits the measuring of the pulse frequency up to 220 heart beats per minute. Interferences which occur within the unstable state are eliminated by the monostable multivibrator.

Preferably, there is at least one filter, designed as band pass amplifier, installed between the receiver and the threshold value switch. In this way, a great part of the interference signals can be filtered out before the signals reach the monostable multivibrator.

The amplification of the amplifier, installed in front of the short-time storage, can be controlled in a manner corresponding to the peak value of the signal stored in the short-time storage at particularly low expense if a field effect transistor is provided in the return circuit of the amplifier. The gate of the field effect transistor is connected with the output of an amplifier at the input of which the peak value of the signals stored in the short-time storage is located. The input of the last mentioned amplifier can be selected at such a high impedance (Z) that it does not affect the stored peak value and, by means of the field effect transistor, the amplification can be changed within a large range and very rapidly.

In order to adapt the device as effectively as possible to the different conditions in the case of different persons, the amplifier controlling the field effect transistor has an adjustable and variable amplification.

The receiver can consist of two or three body electrodes. When using two body electrodes, an impedance transformer is installed subsequent to each of them and when using three body electrodes, only two of them have each installed such an impedance transformer. The third body electrode serves as mass supplier. The outputs of the impedance transformers are connected to a sum-and-difference amplifier. However, the receiver can also comprise an optoelectrical pulse receiver to be preferably placed at the ear.

Below, the invention is explained in detail by means of two exemplified embodiments shown in the drawings, wherein:

DETAILED DESCRIPTION OF A PREFERRED EMBODIMENT

Figure 1:
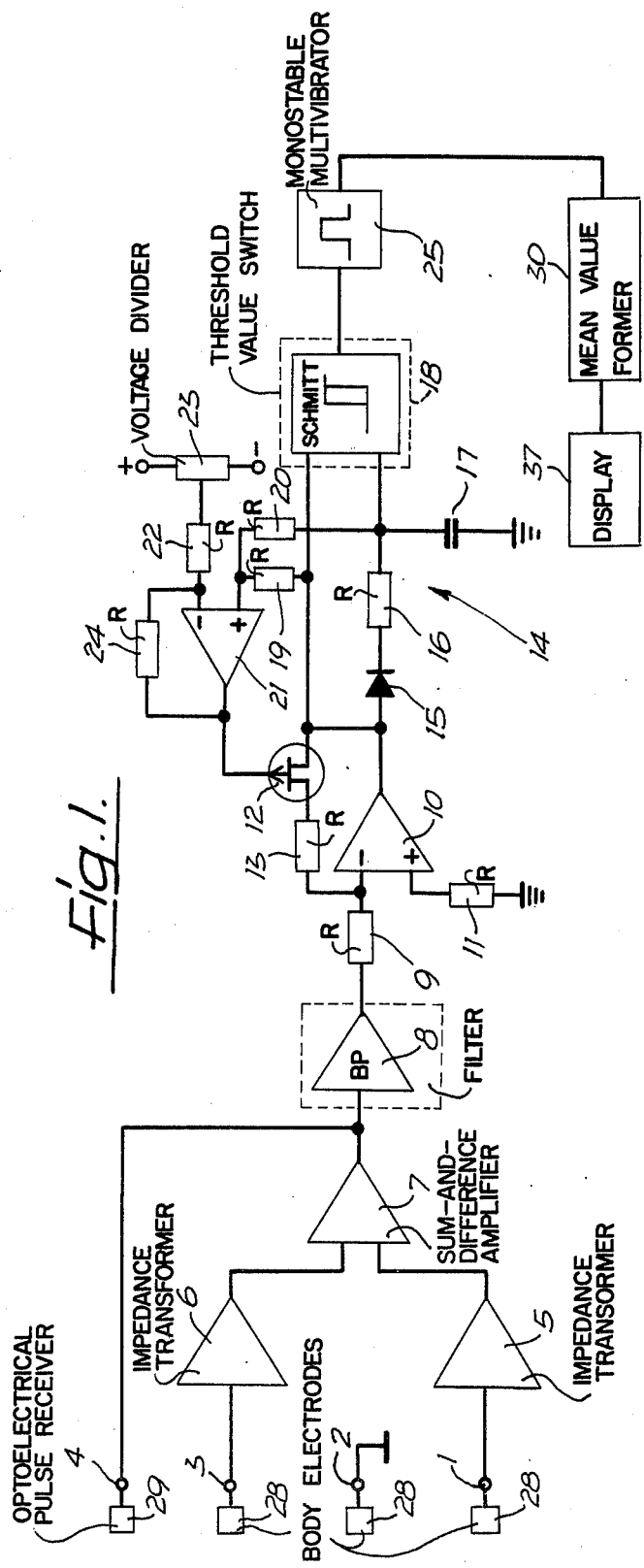
FIG. 1 is a wiring diagram of the first exemplified embodiment.

A device for the production of a sequence of square wave pulses corresponding to the pulse beats of a human being has, as is shown in FIG. 1, four inputs 1, 2, 3 and 4. The input 2 is on ground connection.

Either two or three body electrodes 28 or an optoelectrical pulse receiver 29 can be utilized as receivers. The body electrodes are connected to the inputs 1, 2 and 3, the optoelectrical pulse receiver to the inputs 2 and 4. The inputs 1 and 3 are connected to the two inputs of a sum-and-difference amplifier 7, each through an impedance transformer 5 and 6 each of which comprises one amplifier. The input 4 is connected to the output of the sum-and-difference amplifier 7 subsequent to which a filter constructed as a band pass amplifier 8 is installed.

The signals filtered by the band pass amplifier 8 are supplied, over a coupling resistor 9, to the inverting input of an operational amplifier 10, the non-inverting input of which is connected, via a resistor 11, with ground. The operational amplifier 10 has a return line connecting its output with the inverting input which is formed by the series connection of a field effect transistor 12 and a resistor 13. It is the purpose of the field effect transistor 12 to control changes in the amplification of the operational amplifier 10.

Subsequent to the amplifier with variable amplification formed by the operational amplifier 10 and the variable resistance feed-back, a short-time storage is installed which is designated generally by 14. The short-time storage 14 consists of a diode 15, a resistor 16 and a condenser 17 which are installed in this sequence, whereby the diode is connected to the output of the operational amplifier 10, with its conduction direction as shown in the drawing and the condenser is connected with ground.

The short-time storage 14 is followed by a threshold value switch 18 which, in the exemplified embodiment, is designed as a Schmitt trigger comprising an operational amplifier. Since the threshold value switch 18 should then emit a signal at its output when the peak value of the signal stored in the short-time storage 14 exceeds the threshold value, the one input of the operational amplifier contained in the threshold value switch 18 is connected with the connection between the resistor 16 and the condenser 17. The other input is connected to the output of the operational amplifier 10.

Since the amplification of the operational amplifier 10 is to be controlled as a function of the peak value of the signal stored in the short-time storage, the value of the peak value signal so stored remains constant for the duration it is stored in the short-time storage. A voltage divider comprising the resistors 19 and 20, and which is of a high-impedance character, is connected in parallel to the input of the threshold value switch 18. This voltage divider is also in parallel to the connection in series formed by the diode 15 and the resistor 16. The center pick-up of the voltage divider formed by the resistors 19 and 20 is connected with the non-inverting input of an operational amplifier 21, the inverting input of which is, via a resistor 22, connected at the pickup of a voltage divider 23 and is, via a resistor 24, connected with the output of operational amplifier 21. By means of the voltage divider 23 and a voltage source, which is not shown, the amplification of the operational amplifier 21 can be adjusted and changed. The output of the operational amplifier 21 is connected with the gate of the field effect transistor 12.

Subsequent to the threshold value switch 18, there is a monostable multivibrator 25 at the output of which a sequence of square wave pulses occurs which corresponds to the sequence of pulse beats which are picked up by means of the receiver. The time of the unstable state of the monostable multivibrator 25 has been chosen such that pulse frequencies up to 220 heart beats per minute can be measured. Interferences which occur within the unstable state are eliminated.

Owing to the fact that the amplification of the operational amplifier 10 is controlled as a function of the peak value of the preceding signal stored by means of the short-time storage 14, the peak value of the signals occurring at the output of the operational amplifier is, independently of interfering influences, within a range which makes an additional evaluation possible. Since the amplitude of the signal can be very different in case of different persons, the device can be adjusted to these differences by setting a suitable amplification by the use of the voltage divider 23.

Figure 2:
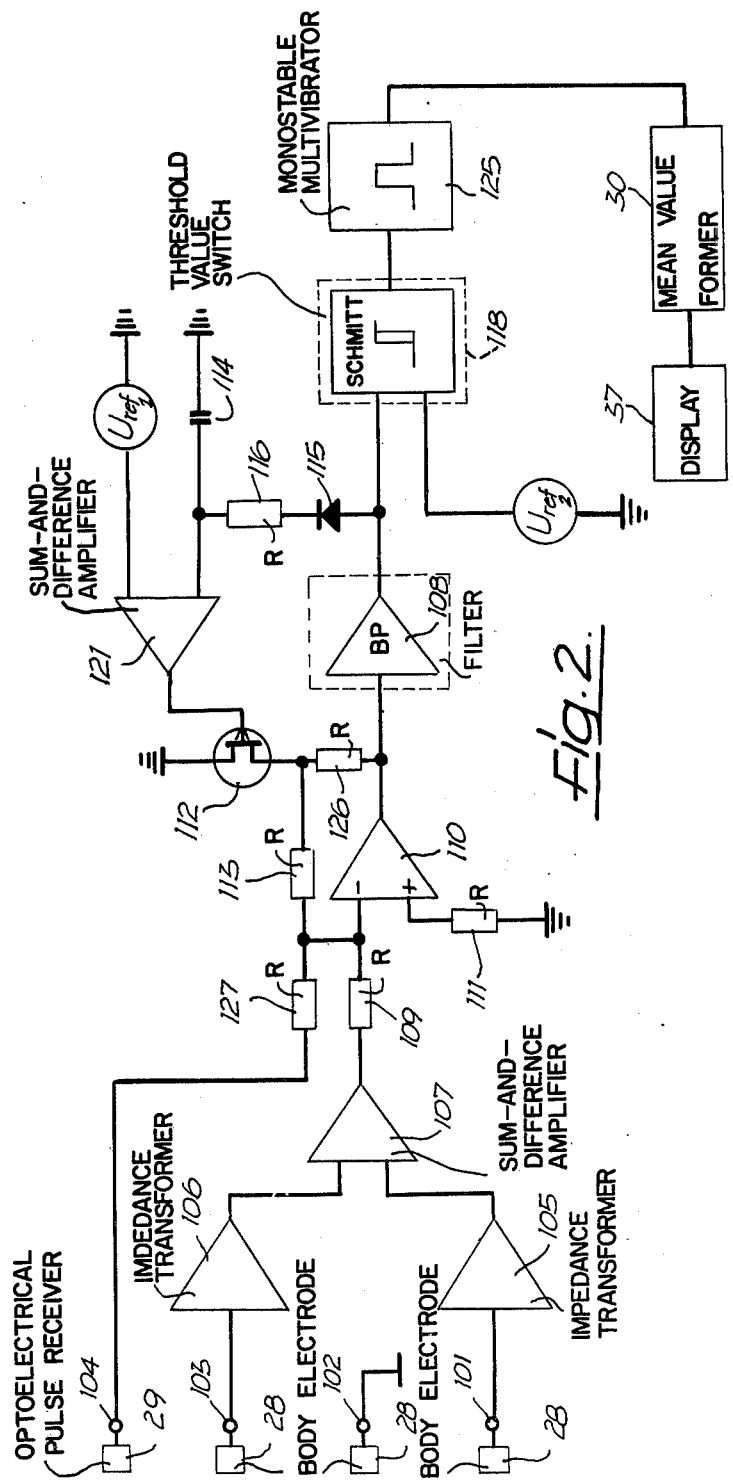
FIG. 2 is a wiring diagram of the second exemplified embodiment.

In the case of the exemplified embodiment shown in FIG. 2, the output of the sum-and-difference amplifier 107, the two inputs of which are connected with the impedance transformers 105 and 106, is connected with the inverting input of the operational amplifier 110 over a coupling resistor 109. Also the input 104 of the receiver 29 is connected to this input via a coupling resistor 127. The non-inverting input of the operational amplifier 110 is connected with the ground through resistor 111.

The operational amplifier 110 has, just as the operational amplifier 10 of FIG. 1, a return line connecting its output with the inverting input. This is formed by a resistor 113 which, on the one hand, is connected to the inverting input and, on the other hand, to the pick-up of a voltage divider which is formed by a fixed resistor 126 and a field effect transistor 112. The voltage divider is installed between the output of the operational amplifier 110 and the ground and this in such a manner that the resistor 126 is connected with the output of the operational amplifier 110 and the field effect transistor 112 with ground.

The output of the operational amplifier 110 is connected with the input of the threshold value switch 118 over a band pass amplifier 108. But also the operational amplifier 110 has the effect of a band pass amplifier.

A peak value short-time storage is connected to the input of the threshold value switch 118 being in contact with the band pass amplifier 108; this peak value short-time storage is formed by a connection in series consisting of the diode 115, the resistor 116 and the condenser 114. The condenser 114 is, on the one hand, connected with ground and, on the other hand, with one input of a sum-and-difference amplifier 121 at the other input of which there is a reference voltage $U_{ref1}$. The output of the sum-and-difference amplifier 121 is connected with the gate of the field effect transistor 112. The condenser 114 is, over the diode 115 and the resistor 116, charged to the peak value of the signal occurring at the output of the band pass amplifier 108 and modulates the field effect transistor 112 as a function of the difference between this peak value and the reference voltage at the other input whereby the potential at the pick-up of the voltage divider for the return of the operational amplifier 110 and thus the amplification degree of this operational amplifier is adjusted to the value obtained by the desired signal amplitude at the output of the operational amplifier 110.

As is shown in FIG. 2, there exists also a reference voltage $U_{ref2}$ at the second input of the threshold value switch 118. The threshold value switch 118 is triggered when the signal occurring at the output of the band pass amplifier 108 reaches the necessary amplitude.

The threshold value switch 118 triggers the monostable multivibrator 125. Each time the monostable multivibrator 125 is triggered, a square wave pulse develops at its output. The time of the unstable state of the multivibrator 125 is determined in such a way that pulse frequencies up to 220 heart beats per minute can still be processed. Interferences which occur as long as the monostable multivibrator 125 is in its unstable stage, are eliminated.

As in the case of the exemplified embodiment according to FIG. 1, the device has four inputs 101 to 104 to which two or three body electrodes 28 or an optoelectrical pulse receiver 29 are connected.

Figure 3:
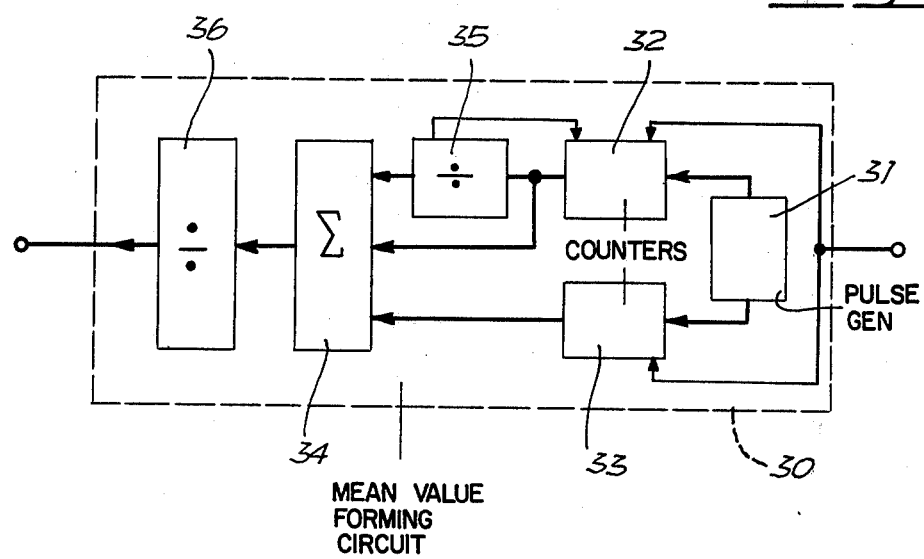
FIG. 3 is a wiring diagram of the device for the formation of the mean value.

As in the case of the exemplified embodiment according to FIG. 1, there is also in the case of that according to FIG. 2, a device for the formation of the mean value, designated by reference numeral 30, and installed subsequent to the monostable multivibrator 125. This device, as shown in FIG. 3, consists of a pulse generator 31, two pulse counters 32 and 33, a summing connection 34 as well as two dividing connections 35 and 36.

The output signals of the monostable multivibrator, the intervals of which in time correspond to the coordinated heart pulse period, are used for the control of the two pulse counters 32 and 33 to which counted pulses i are supplied which are produced by the pulse generator 31 and have a frequency of 50 Hz in the exemplified embodiment.

Since the frequency meter according to the invention indicates the heart pulse frequency in the form of a sliding mean value from 25 heart pulse periods, the counter 32 always counts the number of the counted pulses i which fall into the period of time between the −1st and the 24th heart pulse period. On the other hand, the counter 33 forms continuously the sum of the counted pulses in the period of time between the 24th and 25th heart pulse period. The two sums determined by the counters 32 and 33 are supplied to the summing connection 34 to which is also supplied the negative value of the initial value of the dividing connection 35 which divides the sum formed by the counter 32 by the value 25. Therefore, the following equation is applicable for the initial dimension of the summing connection:

$$\sum_{0}^{25} i = \sum_{-1}^{24} i - \frac{\sum_{-1}^{24} i}{25} + \sum_{24}^{25} i$$

By means of components in the circuit not shown in detail, all those initial pulses of the monostable multivibrator, the period duration of which is under 0.2 second and above 2 seconds, are eliminated.

The summing connection 34 is followed by the dividing connection 36 which, in the exemplified embodiment, determines the magnitude:

$$F = \frac{75000}{\sum_{E=0}^{E=25} i}$$

The magnitude F represents the sliding mean value of 25 heart pulse periods E measured in pulse beats per minute. From this dimension as well as the frequency of the counted pulses and the number of the heart pulse periods used for the formation of the mean value results the value given in the counter.

The dividing connection is designed in such a manner that, per heart pulse period, the value F can only change by one unit up or down. Since the heart pulse frequency also changes correspondingly slowly, additional interfering influences are eliminated in this way.

For the elimination of interfering influences, an additional filter can be provided which forms a time window with the conditions:

$$0.8 \, E_n{-}1 < E_n < 1.2 \, E_{n-1}$$

and eliminates all pulses which do not fall into this time window.

The task of the counters 32 and 33, of the summing connection 34 and of the dividing connections 35 and 36 are advantageously performed by an arithmetic computer with program storage which, for reasons of expediency, consists of an input/output unit, a microprocessor and an ROM/RAM storage. In this connection it is of particular advantage that only two storage places are required for the computation of the sum of the counted pulses.

In the case of the exemplified embodiments, the sliding mean value F is continuously displayed or displayed on call in digital form on a display 37.

Although only preferred embodiments are specifically illustrated and described herein, it will be appreciated that many modifications and variations of the present invention are possible in light of the above teachings and within the purview of the appended claims without departing from the spirit and intended scope of the invention.

What is claimed is:

1. Process for the measuring of the heart pulse frequency, particularly for the measuring of the heart pulse frequency of a moving test person for the purpose of a performance test, comprising the steps of detecting heart pulse signals at the body of the test person, counting the heart pulses, eliminating from said counted heart pulse periods the interval of time of which deviates from the preceding heart pulse by more than 20% in either direction from the magnitude resulting from the period duration of said heart pulse, producing a constant frequency pulse, determining the mean value of the heart pulse frequency from the number of counted pulses of constant frequency which fall into a period of time defined by a predetermined number n of heart pulse periods E not so eliminated by forming a first term corresponding to the sum of the counted pulses within the period of time of $-1$ to $n-1$, forming a second term corresponding to the negative value of the first term divided by the predetermined number n of heart pulse periods E not so eliminated, forming a third term corresponding to the number of counted pulses not eliminated within the period of time $n-1$ to n and forming the sum of said first, second and third terms.

2. Process in accordance with claim 1, including the step of eliminating changes of the mean value of the heart pulse frequency within a heart period of more than a single unit.

3. Process in accordance with claim 1, including the step of amplifying the signals detected at the body of the test person as a function of the peak value of the preceding signal, subsequently, storing said amplified signals as constant values until the next successive signal is detected and triggering, by means of the amplified signals, a threshold value switch for indicating amplified signals of a predetermined magnitude for use in said determining step.

4. A heart pulse frequency meter comprising a receiver for receiving heart pulses, an amplifier connected to the receiver for amplifying the signals produced by the receiver, means connected to said amplifier for forming the mean value of the heart-pulse frequency, said mean value forming means determining the mean value of the pulse frequency over a period of time of n heart pulse periods in view of the number of counted pulses falling within said period of time, said mean value forming means including counter means for determining the counted pulses falling into periods of time $-1$ to $n-1$ and $n-1$ to n, means for eliminating from said mean value forming means heart pulse periods the interval of time of which deviates from the preceding heart pulse by more than 20% in either direction from the magnitude resulting from the period duration of said preceding heart pulse, computing means for computing the mean value based on the counted pulses in the counter means, means connecting said counter means to said computing means and means for displaying the mean value.

5. A heart pulse meter in accordance with claim 4, including means for varying the amplification of said amplifier, short-time constant value storage means connected to said amplifier and to said amplification varying means, a threshold value switch connected to the output of said amplifier and a monostable multivibrator connected to the output of said threshold value switch, the output of said monostable multivibrator being connected to said mean value forming means.

6. A heart pulse meter in accordance with claim 5, wherein the monostable multivibrator has an unstable state, the period of time of which is a value which permits the measuring of the pulse frequency up to a limit value.

7. A heart pulse meter in accordance with claim 6, wherein said limit value is 220 heart beats per minute.

8. A heart pulse meter in accordance with claim 5, including at least one filter comprising a band pass amplifier connected in circuit between the receiver and the threshold value switch.

9. A heart pulse meter in accordance with claim 5, wherein said amplification varying means includes a field effect transistor for varying the feedback to said amplifier, said transistor having a gate, source and drain, a further amplifier having an input and an output, said gate being connected with the output of said further amplifier, said source being connected to the output of said amplifier, said drain being connected to ground, the input of said further amplifier being connected to said short-time constant value storage means for receiving the peak value of the signal stored therein.

10. A heart pulse meter in accordance with claim 5, wherein the receiver comprises at least two body electrodes, each electrode being connected to an impedance transformer, the outputs of said transformers being connected to the inputs of a sum-and-difference amplifier.

11. A heart pulse meter in accordance with claim 5, wherein the receiver comprises an optoelectrical pulse receiver.

12. A heart pulse meter in accordance with claim 5, wherein said amplification varying means includes a field effect transistor for varying the feedback to said amplifier, said transistor having a gate, source and drain, a further amplifier having an input and an output, said gate being connected with the output of said further amplifier, said source being connected to the output of said amplifier, said drain being connected to an input of said amplifier, the input of said further amplifier being connected to said short-time constant value storage means for receiving the peak value of the signal stored therein.

13. Process for the measuring of heart pulse frequency, particularly for the measuring of the heart pulse frequency of a moving test person for the purpose of a perforance test, comprising the steps of detecting a signal at the body of the test person, amplifying the detected signal as a function of the peak value of the preceding detected signal, subsequently storing as a constant value the signal detected at the body of the test person until the next successive signal is detected, triggering, by means of the amplified signal, a threshold value switch for indicating amplified signals having a predetermined magnitude, determining the mean value of heart pulse frequency from the amplified signals indicated by the threshold value switch and displaying the heart pulse frequency.

14. A heart pulse frequency meter comprising receiver for receiving detected heart pulses, an amplifier connected to said receiver for amplifying the signals received by the receiver, means for varying the amplification of said amplifier, short-time storage means connected to said amplifier and to said amplification varying means for storing said signals as constant values, a threshold value switch connected to the output of said amplifier, a monostable multivibrator connected to the output of said threshold value switch, means connected to the output of said monostable multivibrator for determining the mean value of the frequency of said signals, said mean value corresponding to heart pulse frequency and means connected to said determining means for displaying the heart pulse frequency.

* * * * *